United States Patent
Giles

(10) Patent No.: US 9,493,733 B2
(45) Date of Patent: Nov. 15, 2016

(54) CONTAINER ASSEMBLY

(75) Inventor: William Giles, Manistique, MI (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1543 days.

(21) Appl. No.: 12/689,073

(22) Filed: Jan. 18, 2010

(65) Prior Publication Data

US 2011/0174820 A1    Jul. 21, 2011

(51) Int. Cl.
| | | |
|---|---|---|
| C12M 1/22 | (2006.01) | |
| B01L 3/00 | (2006.01) | |
| C12M 1/00 | (2006.01) | |
| C12M 1/30 | (2006.01) | |

(52) U.S. Cl.
CPC ............... *C12M 23/10* (2013.01); *B01L 3/508* (2013.01); *C12M 23/38* (2013.01); *C12M 33/02* (2013.01); *B01L 2300/042* (2013.01); *Y10T 29/53* (2015.01)

(58) Field of Classification Search
CPC .................. C12M 23/10; C12M 23/38; C12M 33/02; B01L 3/508; B01L 2300/042; Y10T 29/53
USPC ........... 435/297.5, 305.4; 220/315, 700, 298, 220/300, 783, 784, 788; 215/44; 29/700
See application file for complete search history.

(56) References Cited

U.S. PATENT DOCUMENTS

| | | | |
|---|---|---|---|
| 4,172,532 A | 10/1979 | Palsson | |
| 5,854,065 A | 12/1998 | Livingston et al. | |
| 5,863,792 A | 1/1999 | Tyndorf et al. | |
| 6,602,704 B1 | 8/2003 | Maxwell et al. | |
| 6,660,494 B2 * | 12/2003 | Schabert et al. | ................ 435/34 |
| 6,969,606 B2 | 11/2005 | Minton | |
| 6,969,607 B2 | 11/2005 | Minton | |
| 7,452,711 B2 | 11/2008 | Daykin | |
| 2005/0189362 A1 | 9/2005 | Muller | |
| 2006/0240549 A1 | 10/2006 | Minton | |
| 2006/0252299 A1 | 11/2006 | Daykin | |
| 2007/0166819 A1 | 7/2007 | Ghosh et al. | |
| 2010/0093075 A1* | 4/2010 | Muller | ........................ 435/305.4 |

FOREIGN PATENT DOCUMENTS

| | | |
|---|---|---|
| CA | 2603244 A1 | 3/2009 |
| EP | 0 171 854 A1 | 2/1986 |
| EP | 0866119 A2 | 9/1998 |
| EP | 0999266 A1 | 5/2000 |
| EP | 1261690 A1 | 12/2004 |
| EP | 1528100 A1 | 5/2005 |

(Continued)

OTHER PUBLICATIONS

Machine Translation of FR2486915. Translated on Dec. 29, 2011.*

(Continued)

*Primary Examiner* — Michael Hobbs
(74) *Attorney, Agent, or Firm* — Lerner, David, Littenberg, Krumholz & Mentlik, LLP

(57) ABSTRACT

A container assembly such as a petri dish or a contact plate for use as a sampling device for microorganisms includes a base member, a lid and a locking mechanism that provides a secure locking engagement between the lid and the base member. The locking mechanism is designed such that does not lock except upon application of a specific intentionally applied compressive force, and which may be readily disengaged from locking engagement without the need for a rotational movement or torsional force.

14 Claims, 8 Drawing Sheets

(56) References Cited

FOREIGN PATENT DOCUMENTS

| FR | 2486915 A1 | 1/1982 | |
|---|---|---|---|
| JP | 2005312317 A | 11/2005 | |
| WO | 9324608 A1 | 12/1993 | |
| WO | WO 2008/141597 A2 * | 11/2008 | ............. C12M 1/22 |

OTHER PUBLICATIONS

Machine Translation of EP1261690A1. Translated on Dec. 29, 2011.*
Definition of cantilever. Dictionary.com. Aug. 7, 2012.*
Wilson, Frederic H. and Ball, William; Determination of Ammonia Inhibition in Fabric Impregnated with Antimicrobials; The Journal of the Association of Official Analytical Chemists, vol. 58, No. 5, 1975, pp. 998-1000.

* cited by examiner

CONTAINER ASSEMBLY

BACKGROUND OF THE INVENTION

1. Field of the Invention

The present invention is directed to a container assembly for use in the sampling and growth of microorganisms. More particularly, the invention is directed to a container assembly having a base and a lid where the lid is removably coupled to the base by a locking mechanism.

2. Discussion of the Related Art

Containers for culturing microorganisms are commonly referred to as petri dishes or contact plates and are well known in the art. These devices typically include a bottom container or base or dish portion for the growth medium and a peripheral side wall. The bottom container is typically used in conjunction with a lid having a top wall and a peripheral side wall that is able to fit over the side wall of the bottom container. Generally, the side wall of the lid forms a loose fit with the bottom container to prevent the lid from binding with the bottom container. A contact plate is a much smaller version of a Petri dish, the dish component of which is pre-loaded with growth medium and is provided with a base for grasping the contact plate so as to permit it to be pressed against a surface to obtain a sample of any microorganism(s) present on the sampled surface. Containers such as these are manufactured by several manufacturers and are readily available.

Contact plates and petri dishes are typically fabricated from polymeric material in mass quantities at a sufficiently low cost as to be disposable after a single use. The dish portion of the contact plate is filled with a generally convex mound of growth medium. With the lid removed, the contact plate is grasped by its base and the mound of growth medium is pressed against a surface to be tested for bacterial and/or fungal contamination. The lid is then replaced and the contact plate is stored in an environment conducive to microorganism growth. A typical contact plate is pre-loaded with growth medium under sterile conditions and packaged for shipment to the end user.

Contact plates and petri dishes for microorganisms are commonly used in large numbers each day by a technician. A technician can use several hundred containers each day to test for various microorganisms. To enable the technician to handle the large number of containers efficiently, the lids must be easily removed and replaced without sticking or binding together. In some instances, it is desirable to have the lid sufficiently loose to enable the technician to remove the lid with one hand while dispensing the sample into the petri dish for testing. Other uses of the petri dish require that the lid be secured to the base to prevent inadvertent separation of the lid from the bottom container but still allow the lid to be removed from the dish with minimal effort.

One problem that often occurs with petri dishes and contact plates during use is the risk of the technician disrupting the growth media after the sample has been taken. This typically results in inaccurate sampling results since unwanted microorganisms are often transferred to the growth media by the inadvertent touching or separation of the lid from the base exposing the growth media to an unintended environment. To reduce the risk of inadvertent contact with the growth media, various methods have been proposed for securing the lid to the base container to prevent inadvertent separation of the lid from the base container. These efforts have often resulted in high frictional forces that can make it difficult to separate the lid from the container. For example, two known designs of contact plates are those that are the subject of U.S. Pat. Nos. 5,854,065 and 6,602,704. Both designs provide a locking mechanism in which the lid and base are held together by a compression fit that may be either too tight to allow ready disengagement between the lid and base container or too loose, which can lead to inadvertent separation of the lid from the base container when handling the contact plate.

Another approach for securing the lid to the base container is the subject of U.S. Pat. Nos. 6,969,606 and 6,969,607 and 7,452,711 which disclose a lockable contact plate wherein the locking members consist of pairs of radial sheaths and tabs. However this approach requires a rotational movement (with a torsional force) of the lid with respect to the base in order to lock or unlock the locking members. A repeated rotational movement using a torsional force can have ergonomic issues for users such as technicians who can handle several hundred containers each day. In addition a rotational locking mechanism can inherently be over torqued/tightened when locked such that an excessive torque force is required to open the locking members.

What is needed therefore is a lockable Petri dish or a lockable contact plate that does not lock except upon application of a specific intentionally applied compressive force, that cannot be over torqued, that provides a secure locking engagement between the lid and the dish, and which may be readily disengaged from the locking engagement without the need for a rotational movement or torsional force.

SUMMARY OF THE INVENTION

The present invention is directed to a container assembly for use in sampling microorganisms. The invention is particularly directed to a container assembly having a base and a lid where the lid can be secured to the base while being readily separable from the base.

According to one embodiment of the present invention, a container assembly comprises a base member having a bottom wall, a continuous side wall; and a lid having a substantially planar top wall, a side wall depending from a peripheral outer edge of the top wall having a distal edge and an inner surface with an inner dimension complimenting an outer dimension of the continuous side wall of the base member; the base member and lid further comprising a snap fit locking mechanism for securing the base member to the lid in locking engagement.

In an additional embodiment of the present invention, a container assembly for use in sampling a surface for the presence of microorganisms, comprises a base having a bottom wall, a side wall, a flange extending outwardly from the side wall, and at least two latch members located on a peripheral edge of the flange; and a lid having top wall, a side wall extending from the top wall and having an inner surface and an inner dimension to be placed on the base and overlie the side wall of the base, and at least two lid key members located on a distal edge of the side wall of the lid, wherein the at least two latch members and at least two lid key members engage to secure the lid to the base.

In another embodiment of the present invention, a method for locking a container assembly comprises the steps of providing a lid having at least two lid key members located on the outer edge of the lid. Providing a base member having a bottom wall, a side wall, a flange extending outwardly from the side wall, and at least two latch members located on a peripheral edge of the flange. Aligning the lid above the base member such that each of the at least two lid key members are directly above each of the at least two latch members. Pressing downward on the lid such that each of the at least two lid key members engages each of the at least two latch members to secure the lid to the base member.

In a further embodiment of the present invention, a method for unlocking a container assembly comprises the steps of providing a lid having at least two lid key members located on the outer edge of the lid, in a locking engagement with a base member having a bottom wall, a side wall, a flange extending outwardly from the side wall, a continuous wall depending from a peripheral edge of the flange in a downward direction and at least two latch members located on the peripheral edge of the flange. Squeezing the base member at a point on the continuous wall below each the latch member to release the lid.

The various features, objects and advantages of the invention will become apparent to those skilled in the art in view of the following detailed description and the annexed drawings which disclose preferred embodiments of the invention.

BRIEF DESCRIPTION OF THE DRAWINGS

The following is a brief description of the drawings in which.

DETAILED DESCRIPTION OF THE INVENTION

It will be readily understood that the components of the present disclosure, as generally described and further illustrated in the figures herein, could be arranged and designed in a wide variety of different configurations. Thus, the following more detailed description, as represented in the figures, is not intended to limit the scope of the disclosure, but is merely a representative of exemplary combinations of the components.

Figure 1:
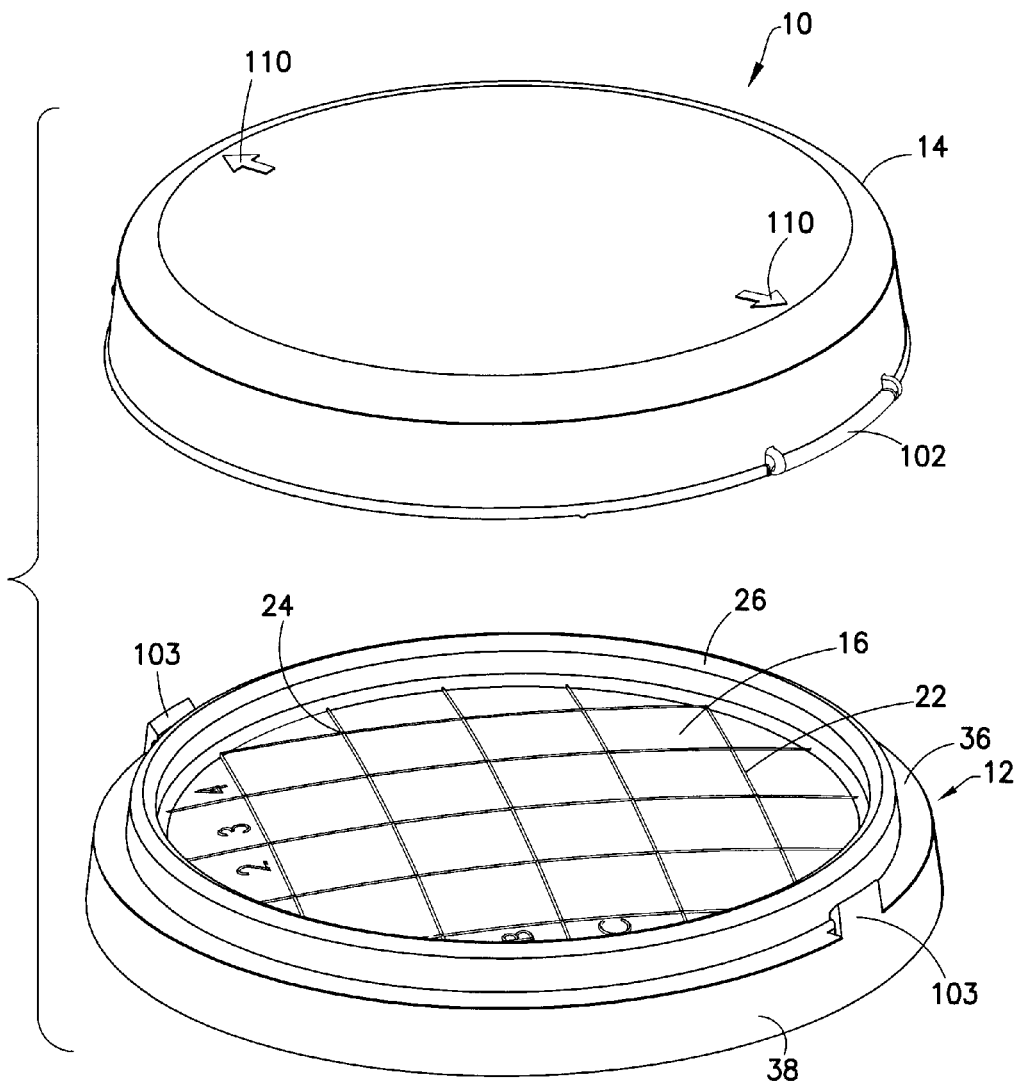
FIG. 1 is an exploded perspective view of the container assembly according to an embodiment of the invention showing the base and lid.

A container assembly 10 having a base member 12 and a lid 14 in accordance with an embodiment of the invention is shown in FIG. 1. Container assembly 10 has a dimension and shape suitable for supporting growth media for growing microorganisms, such as bacteria. In preferred embodiments of the invention, container assembly 10 has a width and a height as commonly used in the industry for devices used in sampling microorganisms. A snap fit locking mechanism 111 is used to retain or lock lid 14 to base 12.

A locking mechanism is provided which when engaged typically enables assembly 10 to be lifted by lid 14 or to be dropped from a height of a laboratory bench (approximately 4 feet) without inadvertent separation of base member 12 from lid 14. A locking mechanism as used herein means a system which locks lid 14 to base member 12 and requires an affirmative locking and unlocking motion or action by a user other than overcoming a frictional retention force which may hold the lid onto the base member in order to detach lid 14 from base member 12. A snap fit lock mechanism further defines the locking mechanism to be one which is engaged/locked or disengaged/unlocked by a non-rotational action or motion without the application of a torsional or rotational force.

Referring to the drawings, container assembly 10 typically has a substantially circular shape as commonly used in the industry. The base member 12 has a bottom wall 16 that forms a support surface suitable for supporting a conventional agar growth medium which can be used for sampling surfaces to determine the presence or absence of microorganisms. In the embodiment illustrated, bottom wall 16 has a slightly convex upper surface 18 and a slightly concave bottom surface 20. In one embodiment, bottom wall 16 includes a plurality of perpendicular intersecting ridges 22 to define a grid system 24. Grid system 24 is provided to facilitate counting of microorganisms as known in the art.

Figure 8:
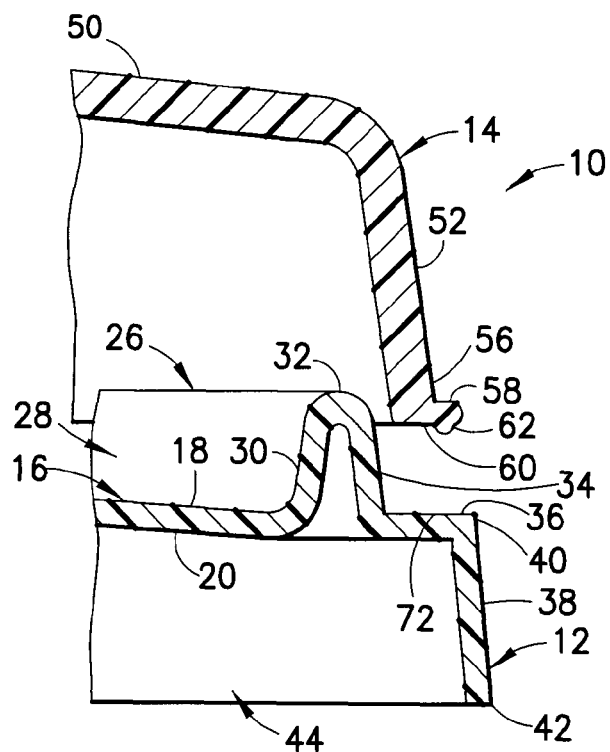
FIG. 8 is a partial cross-sectional side view of the base and lid showing the side wall and the lug on the base of the embodiment as shown in FIG. 1.
Figure 9:
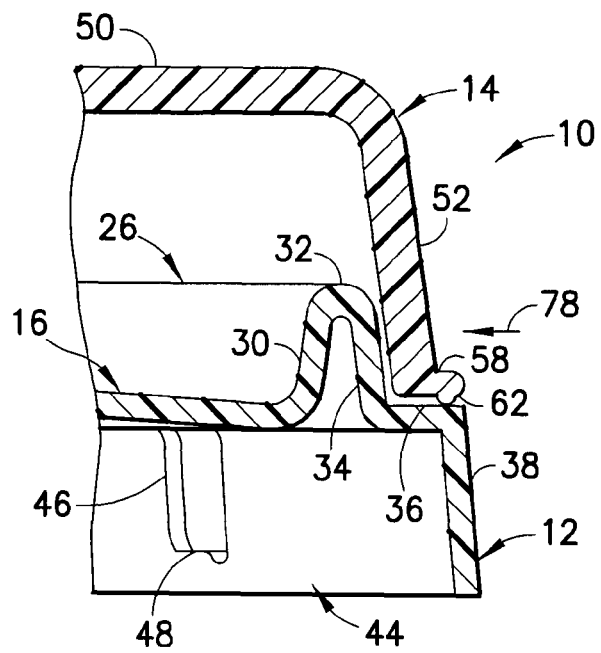
FIG. 9 is a partial cross-sectional view showing the lid fitted on the base of the embodiment as shown in FIG. 1.

Base member 12 includes a side wall 26 that extends away from the plane of bottom wall 16 in a generally upward axial direction with respect to an axial dimension of base member 12 and to define a height of side wall 26. Side wall 26 is a continuous structure that encircles bottom wall 16 and defines an upper cavity 28 in base member 12. Preferably, side wall 26 has an annular or circular shape that extends from the peripheral edge of bottom wall 16 to contain growth medium and receive lid 14. Side wall 26 has a cross-section as shown in FIGS. 8 and 9 with a substantially inverted U-shape formed by an inner wall 30 that extends upward from the peripheral edge of bottom wall 16, a top portion 32 and an outer wall 34 that extends in a generally downward direction from top portion 32. In the embodiment illustrated, inner wall 30 and outer wall 34 are oriented in substantially the same direction and have a slight taper that converge toward top portion 32 to assist in manufacturing and facilitating removal of the base member 12 from the mold used to form base member 12. Base member 12 is typically made as a unitary, single piece from a suitable transparent plastic material such as polystyrene. Typically, base member 12 is made by injection molding so that the taper of inner wall 30 and outer wall 34 facilitate removal of the injection molded part from the mold cavity.

As shown in FIGS. 8 and 9, outer wall 34 has a distal bottom end and a flange 36 extending therefrom. Flange 36 in the embodiment illustrated extends in an outward radial direction with respect to base member 12. Flange 36 in preferred embodiments is continuous and has a substantially annular shape and defines a lid supporting surface with a shape and dimension for receiving and supporting lid 14. Preferably, flange 36 has a uniform width around outer wall 34 and lies in a horizontal plane that is substantially perpendicular to a vertical axis of base 12.

A continuous wall 38 depends from a peripheral edge of flange 36 in a downward direction. As shown, wall 38 extends away from bottom wall 16 and flange 36 in a generally downward direction and defines a circular supporting wall for base member 12. Wall 38 includes an upper edge 40 that is contiguous with flange 36 and extends to a free bottom edge 42. Preferably, wall 38 has a substantially annular shape to stabilize base member 12 when placed on a table or other support surface. In a preferred embodiment, the outer diameter of bottom edge 42 of wall 38 is greater than the diameter of upper edge 40 to assist in stabilizing base member 12 and to assist in stacking and nesting of multiple container assemblies.

Figure 6:
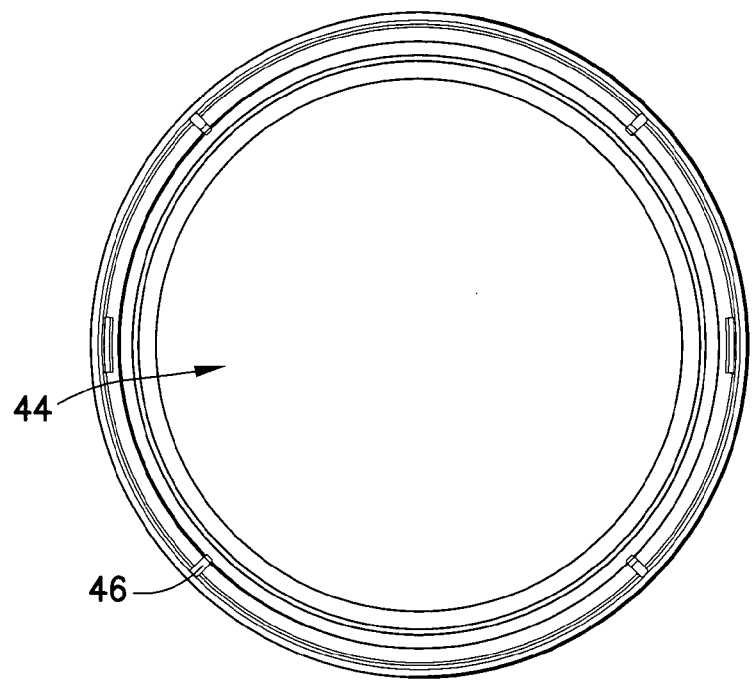
FIG. 6 is a bottom view of the base member of the embodiment as shown in FIG. 1.

Base member 12 has a bottom cavity 44 defined by bottom wall 16 and wall 38. A plurality of ribs 46 as shown in FIG. 6 extend in a generally inward direction from an inner surface of wall 38. Each rib 46 has a bottom surface 48 that is contoured to receive an upper portion of a lid 14 when multiple container assemblies are stacked as shown in FIG. 8. Preferably, bottom surface 48 of ribs 46 have a shape and dimension to contact an upper surface of lid 14. In one embodiment, four ribs 46 are provided and uniformly spaced apart about 90° within bottom cavity 44. The fit between a lid 14 and ribs 46 on an adjacent base member 12 preferably provide a reliable stacking arrangement to resist the stacked container assemblies from sliding laterally with respect to each other. Preferably, ribs 46 and wall 38 have a dimension to receive an upper portion of a lid 14 without binding or sticking so that a container assembly 10 can be lifted from a stack without inadvertent separation of a lid 14 from a respective base member 12.

Figure 2:
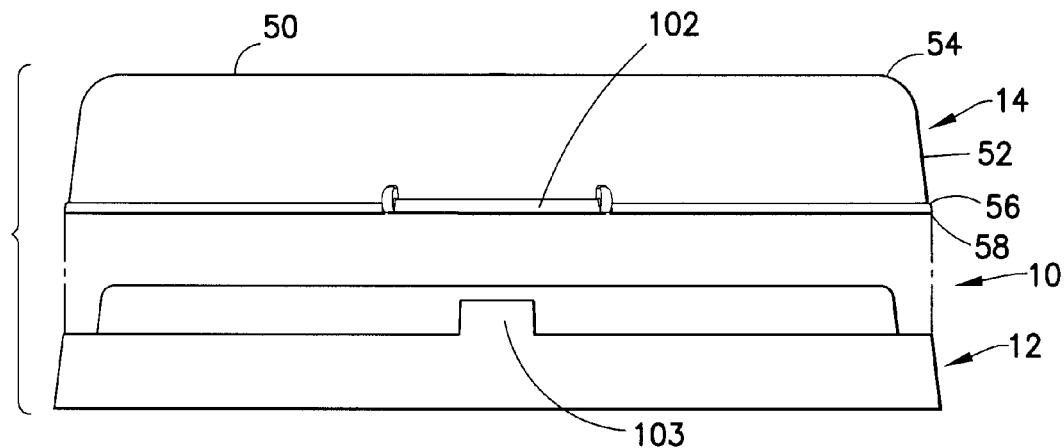
FIG. 2 is a side elevational exploded view of the container assembly according to the embodiment as shown in FIG. 1.
Figure 3:
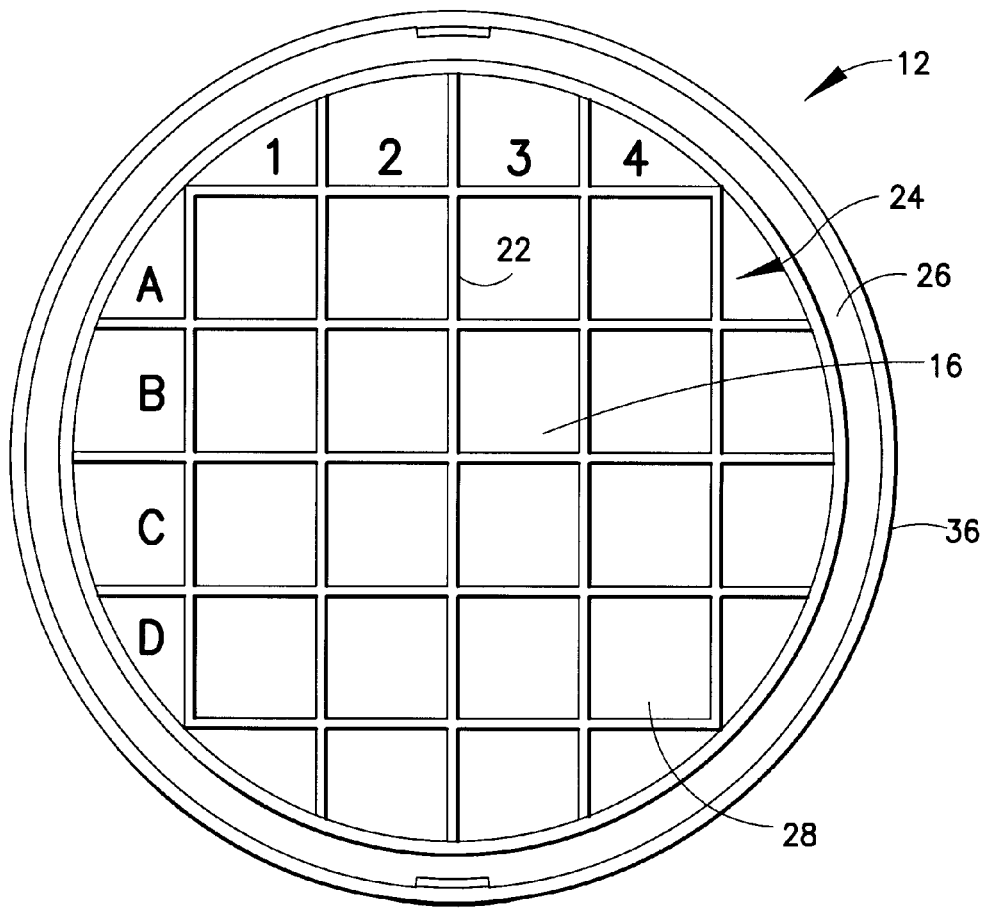
FIG. 3 is a top view of the base according to the embodiment as shown in FIG. 1.
Figure 4:
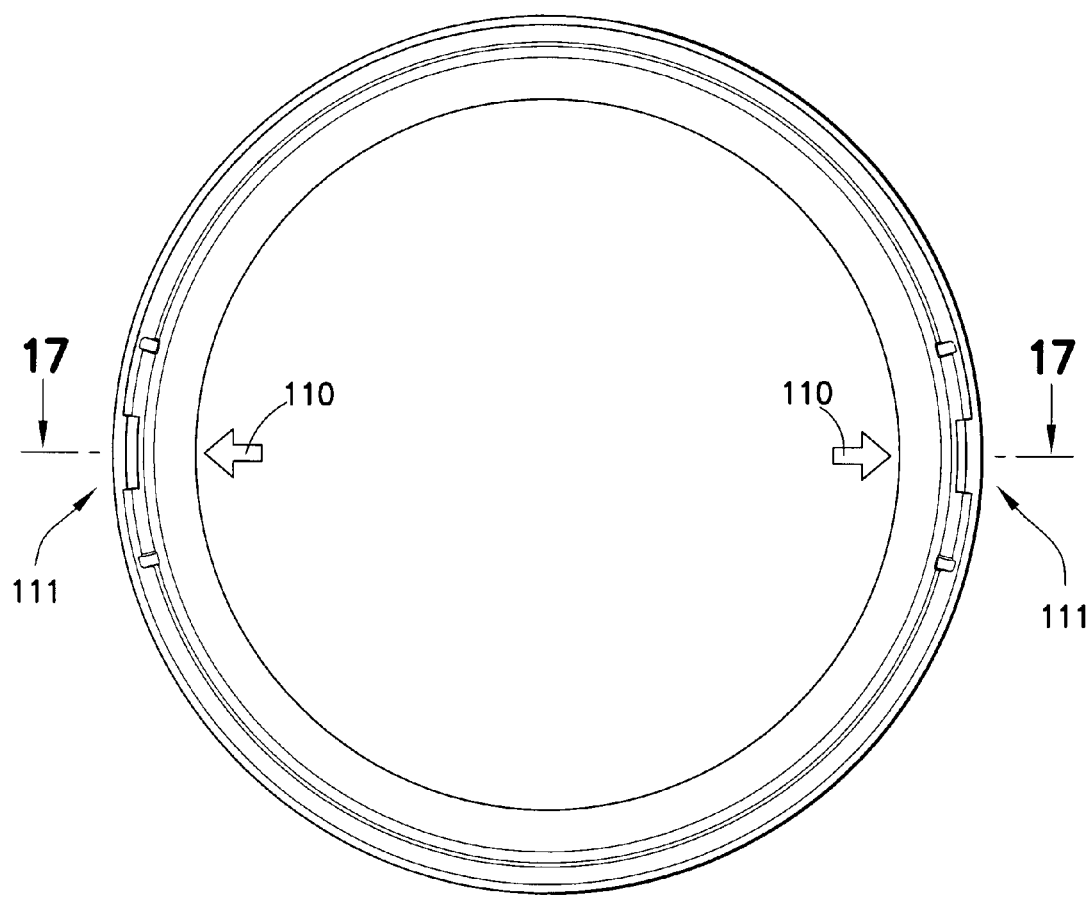
FIG. 4 is a top view of the lid of the embodiment as shown in FIG. 1.
Figure 5:
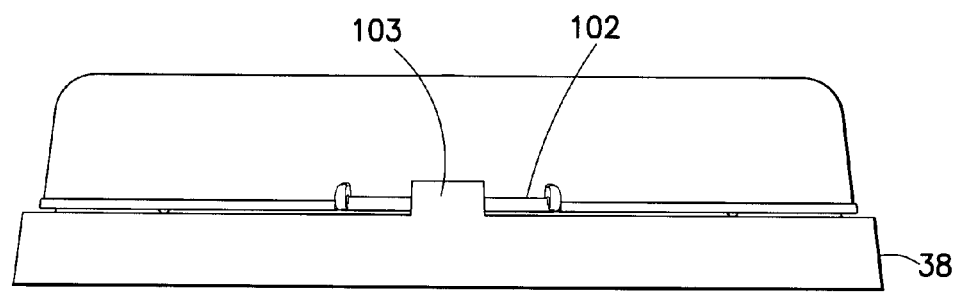
FIG. 5 is a side elevation view of the container assembly of the embodiment as shown in FIG. 1.
Figure 17:
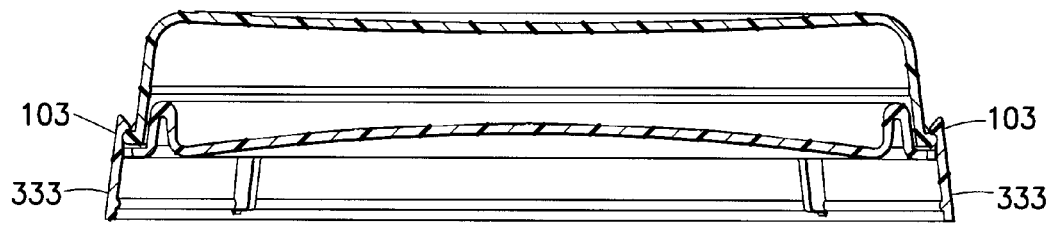
FIG. 17 is a cross-sectional view of the container assembly of the embodiment as shown in FIG. 1.

Lid 14 has a generally planer top wall 50 surface as shown in FIG. 2. Lid 14 is preferably made of a transparent plastic material such as polystyrene that is rigid but is able to provide some limited flex to lid 12 without cracking or breaking. In the embodiment shown, top wall 50 surface has a slightly concave shape as shown in FIG. 17 that is referred to herein as being generally planar. In alternative embodiments, top wall 50 surface can have a slightly convex shape as desired. Lid 14 has a side wall 52 depending from a peripheral outer edge 54 of top wall 50 of lid 14. Side wall 52 extends in a generally downward direction with respect to top wall 50 and has a slightly outward taper. Referring to FIG. 2, side wall 52 has a distal end 56 having an outer dimension that is slightly greater than the outer dimension of top wall 50 so that side wall 52 has a slightly frustoconical shape. In one embodiment of the invention, side wall 52 has a taper of about 7° with respect to a vertical axis of lid 14.

Figure 7:
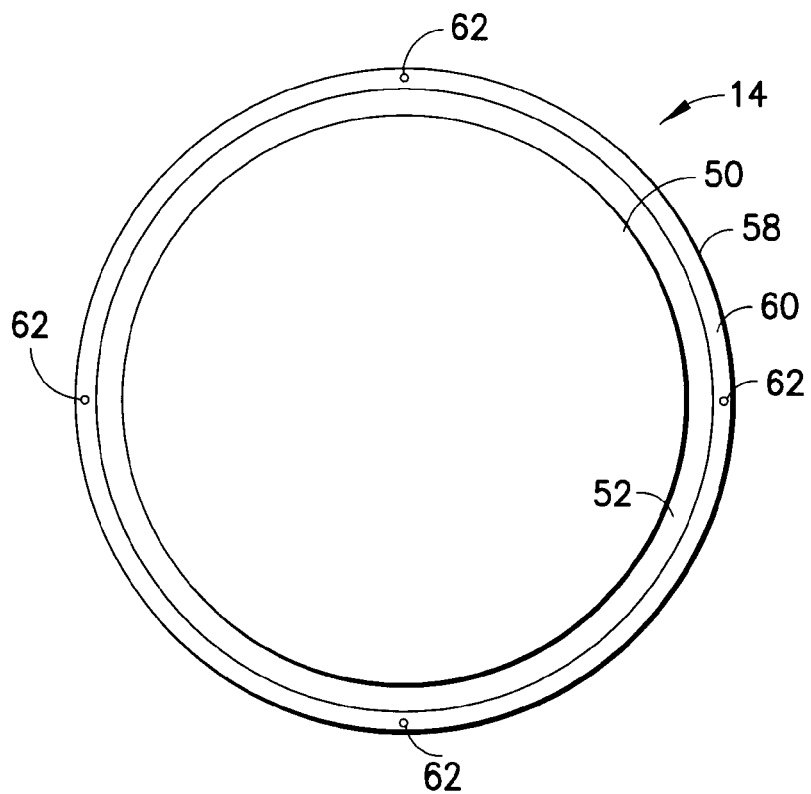
FIG. 7 is a bottom view of the lid of the embodiment as shown in FIG. 1.

Distal end 56 of side wall 52 of lid 14 has a flange 58 that extends radially outward from side wall 52 as shown in FIGS. 2 and 7. Flange 58 has a substantially annular shape with a uniform width. Flange 58 has an outer diameter that is greater than the outer diameter of distal end 56 of side wall 52. Flange 58 provides a visual and tactile indication to the user of the position of lid 14 to reduce the risk of the user inadvertently contacting bottom wall 16 of base member 12 and contaminating the growth media on bottom wall 16.

Flange 58 has a bottom surface 60 that faces in a generally downward direction with respect to the normal orientation of lid 14 when placed on base 12. As shown in FIG. 7, a plurality of protrusions 62 shown as bumps that extend outwardly from bottom surface 60. In a preferred embodiment, protrusions 62 are uniformly spaced apart around the periphery of bottom surface 60 of flange 58. Protrusions 62 have a shape and dimension to space bottom surface 60 of flange 58 from flange 36 of base member 12.

Flange 36 of base member 12 supports side wall 52 of lid 14 when lid 14 is placed on base member 12 as shown in FIG. 9. Protrusions 62 contact flange 36 to form a small gap between flange 36 of base member 12 and flange 58 of lid 14. The small gap allows for air to flow into and out of cavity 28 as may be desired or necessary for many applications in promoting proper growth of microorganisms. The gap formed between flange 36 and flange 58 also prevent a moisture lock or seal from being inadvertently created between lid 14 and base 12 so that lid 14 can be readily separated from base 12.

FIGS. 1 to 17 show a locking mechanism according to an embodiment of the invention for securing the base member 12 and lid 14 in a releasable locking engagement which engages in absence of any rotational movement of the lid 14 in relation to base member 12. The locking mechanism comprises at least two pairs of locking members radially spaced apart from each other, preferably equidistantly (i.e. located 180 degrees apart), wherein each pair of locking members comprises a lid key member 102 and a base latch member 103 adapted to register with each other.

Figure 10:
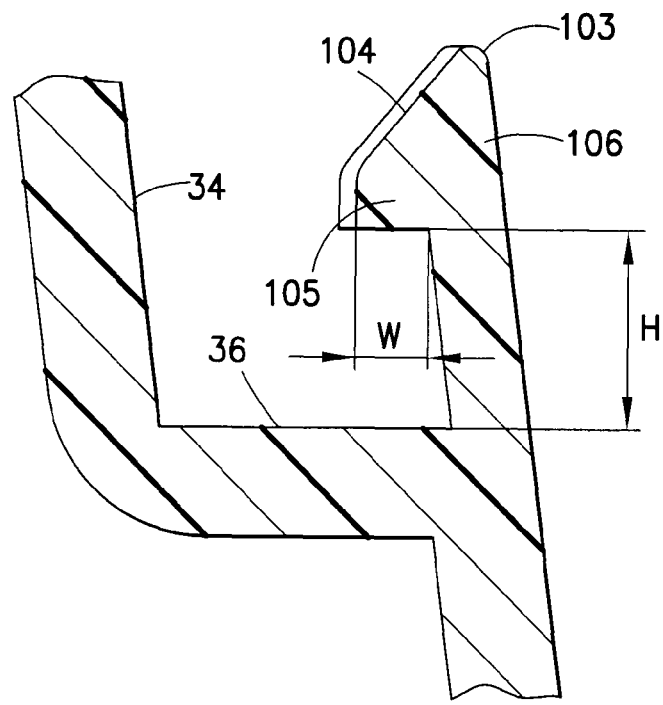
FIG. 10 is a partial cross-sectional view of a latch member of the embodiment as shown in FIG. 1.
Figure 11:
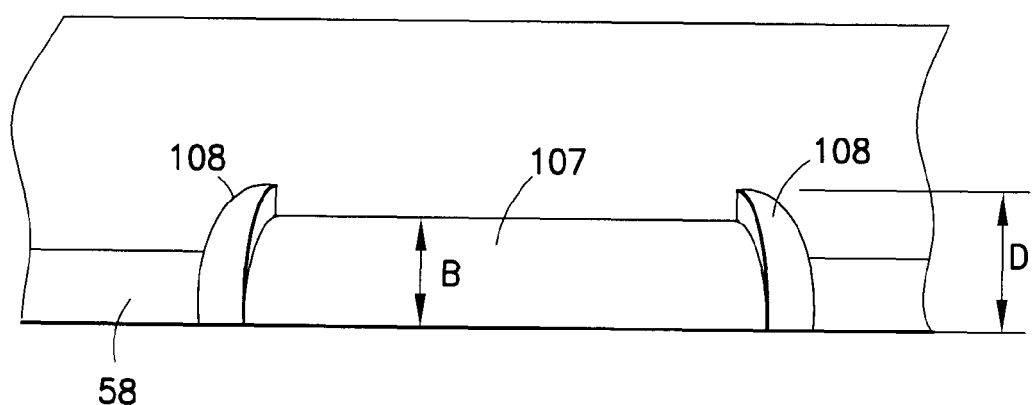
FIG. 11 is a frontal view of a lid key member of the embodiment as shown in FIG. 1.
Figure 12:
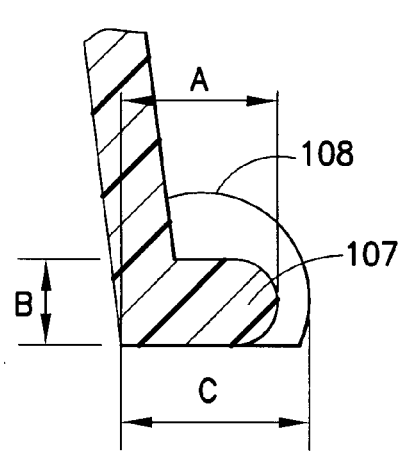
FIG. 12 is a partial cross-sectional view of a lid key member of the embodiment as shown in FIG. 1.

In one embodiment of the invention, each base latch member 103 is integral with the outer surface of wall 38 and flange 36. As shown in FIG. 10 latch member 103 extends from flange 36 in a generally upward axial direction with respect to an axial dimension of base member 12 and has an inward facing ramp section 104 at the top which leads to an undercut 105 and narrow section base 106. Each lid key member 102 is located on the distal end 56 of lid 14 and has a rib section 107 with a vertical stop wall 108 at each end. Rib Section 107 has a greater radial width (A) and height (B) than flange 58. Vertical stop walls 108 have a greater radial width (C) and height (D) than rib section 107.

Figure 13:
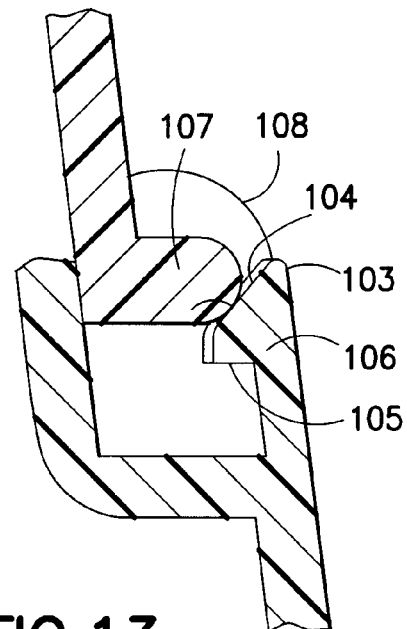
FIG. 13 is a partial cross-sectional view of a lid key member and a latch member of the embodiment as shown in FIG. 1 on initial contact prior to engagement of the locking mechanism.
Figure 14:
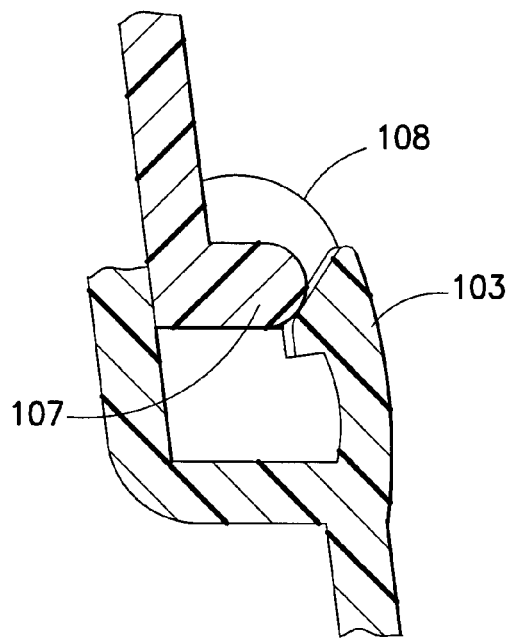
FIG. 14 is a partial cross-sectional view of a lid key member deflecting a latch member of the embodiment of FIG. 1 during engagement of the locking mechanism.
Figure 15:
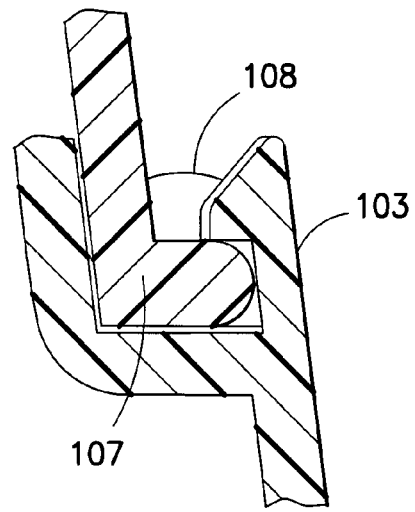
FIG. 15 is a partial cross-sectional view of a lid key member and a latch member of the embodiment as shown in FIG. 1 after engagement of the locking mechanism.
Figure 16:
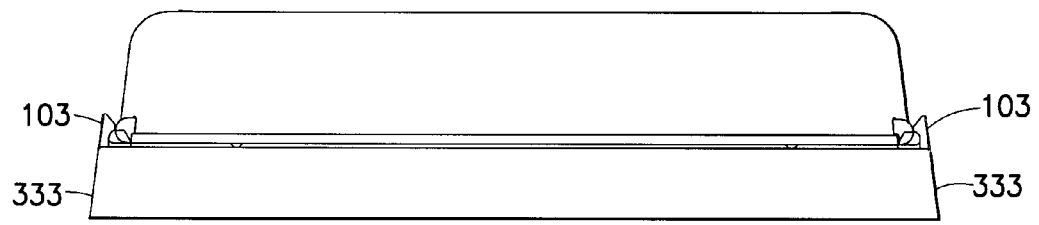
FIG. 16 is a side elevation view of the container assembly of the embodiment as shown in FIG. 1.

Arrows 110 on the upper surface 50 of lid 14 indicate the location of the lid key members 102 on the outer circumference of lid 14, although other shapes or designs of indicators may be used in alternate embodiments. To engage the locking arrangement, lid 14 is placed over base member 12 so that arrows 110 and therefore lid key members 102 are located above and proximate to latch members 103 on the base 12 as shown in FIGS. 1 and 2. Lid 14 is then pushed in a downward or compressive motion such that rib section 107 engages ramp section 104 thereby causing each key member 102 to distort inwardly and/or each latch member 103 to deflect outwards (due to the degree of resiliency imparted by being made from a plastic material such as polystyrene) until rib section 107 slips past ramp section 104 and snaps back into registry with undercut 105 and narrow section 106 thereby returning to their original configuration as shown in FIGS. 13 to 15. This snapping action of the locking members typically provides a clear audible and tactile indication to the user that the locking mechanism is fully engaged and that lid 14 is retained on base member 12, with undercut 105 preventing the vertical movement of rib section 107 and vertical stop walls 108 limiting any rotational movement of the lid 14 in relation to the base member 12.

To disengage or unlock the locking mechanism, wall 38 of base member 12 is compressed inwardly or squeezed at points 333 directly below each of latch members 103, which causes base member 12 and each latch member to resiliently flex outwardly thereby releasing rib section 107 from the undercut 105 of the base latch member. Rib section 107 may also deflect slightly in a similar manner as during the engagement of the locking member in order to slip past undercut 105.

An increase in the length of lid key member 102 allows for a wider tolerance of alignment variation between the lid key member 102 and latch member 103. Rib section 107 has a minimum width dimension equal to the width (W) undercut 105 of latch member 103 and a maximum height dimension equal to the height (H) of narrow section 106 of latch member 103 with a rounded or arcuate cross section to help facilitate slipping past the latch member 103. The retention force of the locking mechanism can be increased by increasing the degree of mating or overlap between rib section 107 and undercut 105. The amount of force necessary to engage the locking mechanism can be controlled by the cross section profile of rib section 107 and the angle of ramp section 104.

Therefore no rotational movement or torsional force is required to engage or disengage the locking mechanism of the present invention. This is a major ergonomic benefit for users such as laboratory technicians, who may have to open and close hundreds of these containers each day.

The misalignment of the locking members allows lid 14 to be placed over and push down onto base member 12 without the engagement of the locking mechanism of this embodiment of the invention. However any attempt to misuse the snap fit locking mechanism of the present invention by subsequently attempting to rotate the lid to align and engage the locking members will fail as the greater radial width (C) and height (D) dimensions of vertical stop walls 108 either prevent the latch member 103 from mating with rib section 107 or will ultimately cause the latch members 103 to break off the base member 12 if an attempt is made to force the latch members 103 around the vertical stop walls 108.

Another advantage of the locking mechanism of the present invention is that the degree or strength of securement between the lid and base is constant and not affected by the application of any additional excessive compressive force applied to the lid on engagement of the locking members, (i.e. the force necessary to disengage the locking members will remain the same regardless of the magnitude of compressive force applied on engagement). Thus on the registration of rib section 108 with undercut 105 any further compressive force will act on flange 36 and not latch member 103. In contrast a rotational locking mechanism can be over torqued/tightened when locked as the locking members will be subjected to any additional excessive torsional force applied to the lid on engagement of the locking members resulting in an increase in the force required to subsequently disengage the locking members or a complete failure of the rotational locking mechanism.

Preferably, container assembly 10 has a dimension to be compatible with other commercially available contact plates and petri dishes and handling apparatus. In one preferred embodiment, base member 12 has a radius of about 2.75 inches and a height of about 0.375 inch. Outer wall 34 of side wall 26 preferably has a radius of about 2.46 inches and a height 82 of about 0.15 inch.

Microbiological media is commonly referred to as culture media or growth media. Growth media is used to support the growth of microorganisms and is available in various formulations depending on the type of organisms that are desired to grow, and is typically differentiated by format. Dehydrated growth media is a dry, powdered version of the growth media. Prepared media is reconstituted dehydrated growth media that is combined with supplements or additives and is available for immediate use by the technician. Prepared media is primarily available in bottled, tubed or plated formats. Agar may be used in the formulation to create a gel-like solid consistency to the growth medium in order to prepare the media for a contact plate or petri dish. Typical formulations of prepared plated media for use in environmental monitoring procedures are based on Tryptic Soy Agar with or without neutralizing agents such as lecithin and polysorbate, Sabouraud Dextrose Agar with or without neutralizing agents such as lecithin and polysorbate, and DE Neutralizing Agar.

Contact or RODAC plates are typically used to assess the efficacy of cleaning and sanitation procedures as part of the overall microbiological monitoring program. The growth media in contact plates forms a convex or domed upper surface, thereby allowing intimate contact between the media and a flat surface.

The process of obtaining a sample using a contact plate according to an embodiment of the invention is as follows. Typically, the growth media contained in a contact plate requires refrigeration. Prior to use, a technician will remove the plate from refrigeration and allow the plates to warm to room temperature in the original packaging. After warming, the technician will open the original packaging in a clean, closed room. The technician will remove the number of plates required for sampling and reseal the package. At this point, the technician may label the plate with a unique identification number or barcode.

The technician will then transport the plates into the room or area to be tested such as a disinfected manufacturing environment. It should be noted that the contact plate locking members typically will be misaligned prior to use such that the lid will not be locked onto the base member. Using one hand, the technician will remove the top of the plate, holding the bottom of the plate with thumb and second finger. The technician then slowly rolls the plate over the sample surface; with the index finger will being used to press the growth media upper surface firmly against the test surface to ensure that the entire growth media upper surface intimately contacts the test surface. After sampling, the lid will be placed on top of the media filled base. The technician then has the option of using the arrows on the top wall of the lid to align the locking members, then pressing down to lock the lid to the base or to misalign the locking members to simply close the lid over the base without locking. The technician will capture date of the sampling location, time and plate used.

This process is then repeated until the requisite number of locations has been sampled. The plates are then returned to the laboratory where they are incubated at specified temperature for a defined period of time. At a set schedule, the plates will then be reviewed for growth by visually inspecting for colony forming units (CFUs). If CFUs are present within in the specific time of incubation, the technician may gram stain the colonies or subculture another media type or use an automated system to identify the microorganism. If growth is negative or once the organism has been identified, plates are discarded as biohazardous waste.

The foregoing description is intended to be exemplary of a preferred embodiment of the invention. It will be understood by those skilled in the art that various changes and modifications to the disclosed embodiment can be made without departing from the purview and spirit of the invention as defined in the appended claims.

What is claimed is:

1. A container assembly comprising:
    a base member having a bottom wall, and a continuous side wall;
    a lid having a substantially planar top wall, a side wall depending from a peripheral outer edge of said top wall having a distal edge and an inner surface with an inner dimension complimenting an outer dimension of said side wall of said base member; and
    a snap fit locking mechanism for securing said base member to said lid in locking engagement in response to a compressive force but not a rotational force, said snap fit locking mechanism including at least one pair of locking members, each said pair of locking members including:
    a lid key member and a base latch member,
    wherein, said lid key member is located on said distal edge of said lid,
    wherein, said base latch member is located radially outwardly from said side wall of said base member so as to define a gap therebetween, said base latch member being fixed at one end to said base member so as to be resiliently deflectable,
    wherein, said lid is emplaceable on said base member with said side wall of said lid encircling said side wall of said base member, and
    wherein, with emplacement of said lid on said base member, each said lid key member is caused to pass through corresponding said gap as the lid is advanced into contact with the base member with resilient displacement of corresponding said base latch member, interengagement between said lid key member and said base latch member causing said lid to be maintained on said base.

2. The assembly of claim 1, wherein said base further comprising a flange extending in a radially outward direction from said side wall of said base, wherein each said base latch member is located on a peripheral edge of said flange.

3. The assembly of claim 1, wherein each said base latch member further comprises a ramp section, an undercut and a narrow section base.

4. The assembly of claim 3, wherein each said lid key member further comprises,
    a rib section having a first end and a second end, and
    a vertical stop wall at each of said first and second end of said rib section wherein the vertical stop wall prevents said lid key member from interengagement with the base latch member by rotational force.

5. The assembly of claim 4, wherein each said rib section is held in locking engagement by said undercut of each said latch member.

6. The assembly of claim 1, wherein the type of force required to engage said snap fit locking mechanism consists of a compressive force.

7. The assembly of claim 1, wherein said snap fit locking mechanism comprises two pairs of locking members.

8. The assembly of claim 7, wherein said two pairs of locking members are radially spaced approximately 180 degrees apart.

9. The assembly of claim 1, wherein said base member comprising a growth media.

10. The assembly of claim 9, wherein said growth media comprising Tryptic Soy Agar.

11. The assembly of claim 2, further comprising a wall depending downwardly from said flange.

12. The assembly of claim 11, wherein at least one said base latch member extends upwardly from said flange away from said downwardly depending wall.

13. The assembly of claim 12, wherein at least one said base latch member is aligned with said downwardly depending wall.

14. The assembly of claim 1 wherein the lid key member comprises two vertical stop walls disposed at either end of a rib portion, wherein the gap defined by the base latch member receives the rib portion as the lid is advanced into contact with the base member such that the base latch member is disposed between the two vertical stop walls wherein the two vertical stop walls prevent the base latch member from being disengaged from the lid key member by rotation of the lid with respect to the base member.

* * * * *